United States Patent [19]
Lane et al.

[11] Patent Number: 6,060,248
[45] Date of Patent: May 9, 2000

[54] PROCESS FOR SELECTING ANTI-SENSE OLIGONUCLEOTIDES

[75] Inventors: Michael J. Lane, Baldwinsville, N.Y.; Albert S. Benight, Schaumburg, Ill.; Brian D. Faldasz, Maynard, Mass.

[73] Assignee: Tm Technologies, Inc., Woburn, Mass.

[21] Appl. No.: 09/028,201

[22] Filed: Feb. 23, 1998

Related U.S. Application Data

[60] Provisional application No. 60/038,796, Feb. 24, 1997.

[51] Int. Cl.[7] .................................................... C12Q 1/68
[52] U.S. Cl. .................................................... 435/6
[58] Field of Search .................................................... 435/6

[56] References Cited

U.S. PATENT DOCUMENTS

| | | | |
|---|---|---|---|
| 5,496,698 | 3/1996 | Draper et al. | 435/6 |
| 5,525,468 | 6/1996 | McSwiggen | 435/6 |

FOREIGN PATENT DOCUMENTS

| | | |
|---|---|---|
| WO 97/27325 | 7/1997 | WIPO . |
| WO 97/27327 | 7/1997 | WIPO . |
| WO 97/27331 | 7/1997 | WIPO . |

OTHER PUBLICATIONS

Hyndman et al. Software to determine optimal oligonucleitide sequences based on hybridization simulation data. Biotechniques vol. 20 pp. 1090–1096, 1996.

Crooke, S.T., "Progress Toward Oligonucleotide Therapeutics: Pharmacodynamic Properties," *FASEB J.*, vol. 7, pp. 533–539 (1993).

Kawasaki, A.M. et al., "Uniformly Modified 2'–Deoxy–2'–fluoro Phosphorothioate Oligonucleotides as Nuclease–Resistant Antisense Compounds with High Affinity and Specificity for RNA Targets," *J. Med. Chem.*, vol. 6, No. 7, pp. 831–841 (1993).

Monia, B.P. et al., "Evaluation of 2'–Modified Oligonucleotides Containing 2'–Deoxy Gaps as Antisense Inhibitors of Expression," *J. Biol. Chem.*, vol. 268, No. 19, pp. 14514–14522 (1993).

*Primary Examiner*—John S. Brusca
*Attorney, Agent, or Firm*—Lahive & Cockfield LLP

[57] ABSTRACT

Methods for identifying a site on a nucleic acid sequence having a desired free energy variability are disclosed. The methods are useful for, e.g., selecting antisense oligonucleotides, e.g., for therapeutic use.

3 Claims, 3 Drawing Sheets

6,060,248

PROCESS FOR SELECTING ANTI-SENSE OLIGONUCLEOTIDES

RELATED APPLICATIONS

This application claims the benefit of priority under 35 U.S.C. 119(e) to co-pending U.S. provisional application Ser. No. 60/038,796, filed Feb. 24, 1997, the entire contents of which are hereby incorporated by reference.

FIELD OF THE INVENTION

This invention relates to a means of selecting nucleotide sequences having a selected value for free energy variance. The methods allow for selecting anti-sense oligonucleotides, for use e.g., as pharmacological agents, from a set of candidates, e.g., those provided by a given nucleic acid, e.g., an mRNA.

BACKGROUND OF THE INVENTION

Antisense therapy involves the administration of exogenous oligonucleotides that bind to a target nucleic acid, typically an RNA molecule, located within cells. The term antisense is so given because the oligonucleotides are typically complementary to mRNA molecules ("sense strands") which encode a cellular product. The ability to use anti-sense oligonucleotides to inhibit expression of mRNAs, and thereby to inhibit protein expression in vivo, is well documented. However, selection of an appropriate complimentary oligonucleotide (or oligonucleotides) to a given mRNA is not always simple (see, e.g., Crooke, S. T. *FASEB J.* 7: 533–539 (1993), incorporated herein by reference). Antisense agents typically need to continuously bind all target RNA molecules so as to inactivate them or alternatively provide a substrate for endogenous ribonuclease H (Rnase H) activity. Sensitivity of RNA/oligonucleotide complexes, generated by the methods of the present invention, to Rnase H digestion can be evaluated by standard methods (see, e.g., Donia, B. P., et al., *J. Biol. Chem.* 268 (19):14514–14522 (1993); Kawasaki, A. M., et al., *J. Med. Chem.* 6(7):831–841 (1993), incorporated herein by reference).

SUMMARY OF THE INVENTION

Prior art methods do not provide efficient means of determining which complimentary oligonucleotides to a given mRNA will be useful in an application. Shorter (15–200) base anti-sense molecules are preferred in clinical applications. In fact, a minimum of 15 base anti-sense oligonucleotides is preferred. The invention includes methods for selecting desired anti-sense oligonucleotides from the set of candidates provided by any given nucleic acid, e.g., an mRNA. In particular, the invention provides a means of determining desired, e.g., sequence positions, e.g., those which present a desired level of free energy variations on the mRNA to design anti-sense oligonucleotides against thus reducing the empiricism currently employed.

In one aspect, the invention features a method of identifying a site on a nucleic acid sequence having high free energy variability. This allows determination of sites which are preferred for oligonucleotide, e.g., antisense, binding. The method includes some or all of the following steps:

providing a nucleotide sequence, e.g., sequence from a target gene;

casting the nucleotide sequence as the free energy as a function of base pair position;

calculating the free energy of X windows centered on a base pair for a plurality of base pairs from the nucleotide sequence for every, or at least a plurality of window sizes between 2 and Y, where Y is an integer between 3 and 1,000, more preferably between 2 and 100;

for each window size, constructing a free energy distribution along the sequence, preferably normalizing the distribution to a standard scale (to account for the fact that the free energy is proportional to window size) (this calculation gives the results which can be plotted as shown in FIG. 1);

finding the mean normalized free energy values for all windows for each base pair position(this gives results which can be plotted as in FIG. 2. It also represents the l"carrier");

subtracting the mean value for a position and provide the deviation from the mean of each base position to determine those sequence which show high variability. The results can be plotted as in FIG. 3 (point "a" in FIGS. 2 and 3 corresponds to high variability).

In certain embodiments, free energy values are calculated for a plurality of window sizes at at least Z percent of the base of the nucleotide sequences, wherein Z is at least 5, 10, 20, 30, 40 , 50, 60, 70, 80, or 90% of the base pairs of the nucleotide sequence.

In another embodiment, the invention provides a method of identifying an optimized ligand binding site on a nucleic acid sequence. The method includes the steps of providing a nucleic acid sequence; calculating a free energy value for at least two window sizes at each of a plurality of base pairs of the nucleic acid sequence; normalizing the free energy values for each window size at each base pair to a standard scale; and calculating a deviation of each normalized free energy value at a base pair from a mean normalized free energy value at the base pair; and selecting a base pair at which a large deviation from the normalized free energy value is calculated, relative to at least one other base pair; such that an optimized ligand binding site on the nucleic acid sequence is identified.

In certain embodiments, free energy values are calculated for a plurality of window sizes at at least Z percent of the base of the nucleotide sequences, wherein Z is at least 5, 10, 20, 30, 40, 50, 60, 70, 80, or 90% of the base pairs of the nucleotide sequence.

In certain embodiments, free energy values are calculated for at least N window sizes at each of the plurality of base pairs, wherein N is at least 2, 5, 10, 15, 20, 30, 40, or 50 window sizes.

In another aspect, the invention provides for a method for determining preferred anti-sense sequence compliments within a predefined RNA sequence; these are generally high variability sequences.(As used herein high variability can be a relative parameter, e.g., relative to other variability in the sequence. Alternatively it can be relative to a predefined value).

In another aspect, the invention provides for sets (e.g., sets of 2, 3, 4 or more) of sequences, e.g., anti-sense oligonucleotides, of an optimal duplex free energy or variability but variable length at the sites of anti-sense candidates within candidate regions.

In another aspect, the invention provides sets of isoenergetic, or isovariable, oligonucleotides, e.g., anti-sense candidates of a set length within a candidate region.

In yet another aspect, the invention provides for establishing oligonucleotides, (e.g., sets of 2, 3, 4 or more) oligonucleotides, e.g., anti-sense oligonucleotides ,of a pre-selected melting temperature, Tm within candidate regions.

Generally, the method allows for identification, choosing, and matching of sequences with desired free energy variability characteristics.

Methods of the invention can be used for any of the following:

Determining the best anti-sense candidate regions, or sub-sequences, within any given anti-sense target. Such sequences exhibit wide variation in average energy as a function of increasing length.

Designing desirable attributes such as Tm, free energy and length coupled with sequence composition to arrive at the best anti-sense oligonucleotide candidates 10–200 bases in length including the pre-identified candidate regions.

Providing compositions of sequence which display the identified variation in sequence composition with changing (e.g., increasing) window size.

Any method of the invention can include providing a sequence, e.g., by synthesizing (by chemical or biochemical methods), or by placing in a reaction mixture which includes a carrier, e.g., a liquid, e.g., water.

DETAILED DESCRIPTION OF THE INVENTION

Figure 1:
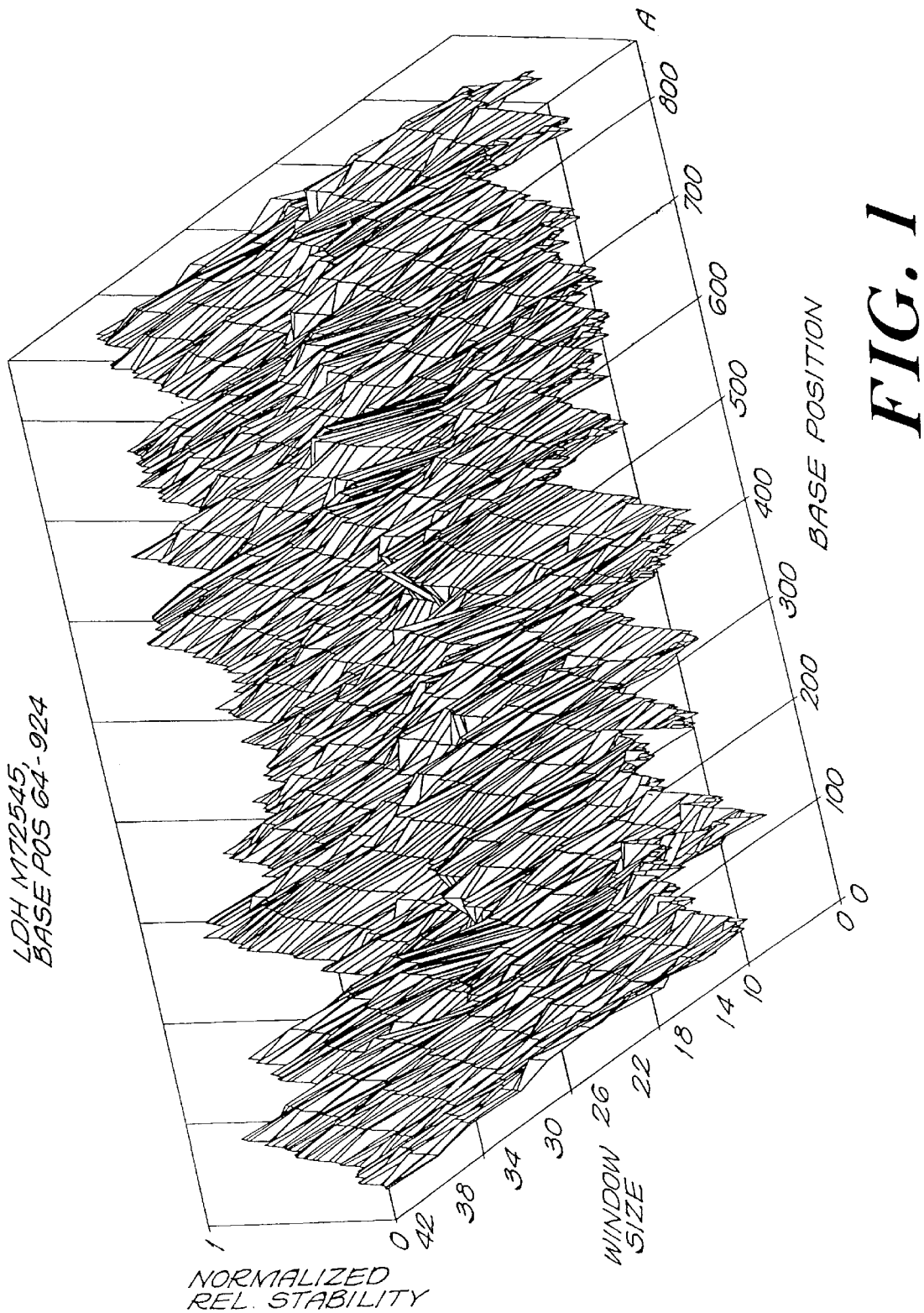
FIG. 1 is a plot of normalized energy as a function of window size and position along a representative DNA sequence.

The invention provides a method(s) for determining base position(s) on a preselected mRNA sequence where best hybridization of an oligonucleotide will occur. Note that the mRNA may be a pre-mRNA (hnRNA) thus containing untranscribed regions to be spliced out and that included in this mRNA/pre-mRNA are a variety of control sequences which allow binding of various cellular components.

For example, if one were to approach the problem of anti-sense design randomly on, for example, a 1000 base target mRNA molecule, then one could pick a set length oligonucleotide, e.g., 30 bases, and synthesize a thirty-mer starting at position 1 of the mRNA and complimentary to positions 1–30 of the mRNA, followed by synthesis of a second thirty-mer starting at position 2 and ending at position 31. This iterative process of synthesis followed to its conclusion results in [1000 base mRNA−2(30 base anti-sense length)+2]=942 thirty base anti-sense oligonucleotides. Similarly, of course one might also select nineteen-mers as the optimal length resulting in [1000 base mRNA−2(19 base anti-sense length)+2]=964 nineteen-base anti-sense oligonucleotides.

In fact, one could synthesize all such complimentary oligonucleotides of length less than the mRNA length and try to inhibit protein synthesis with each in an attempt to find the best anti-sense oligonucleotide for a given mRNA. However, in practice this approach would be an enormous undertaking. Clearly the process of selecting an anti-sense oligonucleotide of length suitable for large scale use as a pharmaceutical while showing in vivo activity would be simplified by identifying the "best" mRNA sequence position to target an anti-sense oligonucleotide against.

The method is described below with reference to data from a representative target nucleic acid sequence (LDH M72545, base positions from 64–924; the sequence is available through GENBANK).

The algorithm for determining relatively "reactive" sites along genomic DNA is based on a representation of duplex DNA in terms of its sequence dependent melting free-energy. This provides DNA sequence as energy contours, that when scrutinized in the proper way, can lead to direct determination of specific sites that are optimum for targeting by anti-sense therapeutic agents.

There are six steps to the current method with at least one step (4) being considered optional:

(1) Free-Energy Representation of DNA Sequences: For a DNA sequence comprised of N base pairs (bps), each bp i can be assigned a melting free-energy value, $\Delta G_i$, $$\Delta G_i = \Delta G^{H-B}{}_i + (\Delta G^s{}_{i,i-1} + \Delta G^s{}_{i,i+1})/2$$

Where $\Delta G^{H-B}{}_i$ is the free-energy of hydrogen bonding that typically can take on only two values (for A-T or G-C type bps) and $\Delta G^s{}_{i,i-1} + \Delta G^s{}_{i,i+1}$ are the nearest-neighbor sequence dependent stacking free-energies for the stacking interactions between bp i and bps i+1 and i−1. Utilizing this equation each bp can be assigned a free-energy of melting.

(2) Construction of Free-Enerlgy Windows: In this procedure, windows of bps containing from 2 to 200 bps are individually examined. For each window size, starting at bp 1, the added free-energy of the bps in the window are summed and plotted as the first point. The window is then moved over one bp and the free-energy of the new window that contains the free-energy of a new bp and not the free-energy of the first bp of the previous window and all the intervening bps, is determined. The process is continued until the last window reaches the end of the DNA sequence under consideration. Formally for each window size, j =10–42 bps starting at bp s=1, N−j+1 the free-energy of each window is given by, $$\Delta G_j{}^w = \Sigma_{i=s,j+s-1}(\Delta G_i)$$

Thus, plotting the values of $\Delta G_j{}^w$ vs. bp position s results in an energy contour for that particular window size, j. Since the magnitude of $\Delta G_j{}^w$ increase with the size of j, relative features of energy contours constructed for different window sizes are difficult to compare directly.

(3) Direct Comparisons of Energy Contours Constructed with Different Window Sizes: To facilitate such a direct comparison the values of $\Delta G_j{}^w$ determined for different values of j are normalized relative to the maximum free-energy difference of any two windows of size j. Thus the normalized free-energy for each window is given by $$<\Delta G_j{}^w < = |(\Delta G_j{}^w - \Delta G_j{}^w(\min))|/|(\Delta G_j{}^w(\max) - \Delta G_j{}^w(\min))|$$

Where $\Delta G_j{}^w(\max)$ and $\Delta G_j{}^w(\min)$ are the maximum minimum and free-energies observed for all the windows along the sequence of size j. Now the free-energy contours constructed with different window sizes consist of a distribution of relative free-energies with values between 0 and 1 vs. bp position.

FIG. 1 is a plot of normalized energy as a function of window size and position along the representative DNA sequence (LDH M72545, base positions from 64–924). The window size was varied over a range from 10 to 42 for each position, and the energy profile for each base position and window size was plotted.

Figure 2:
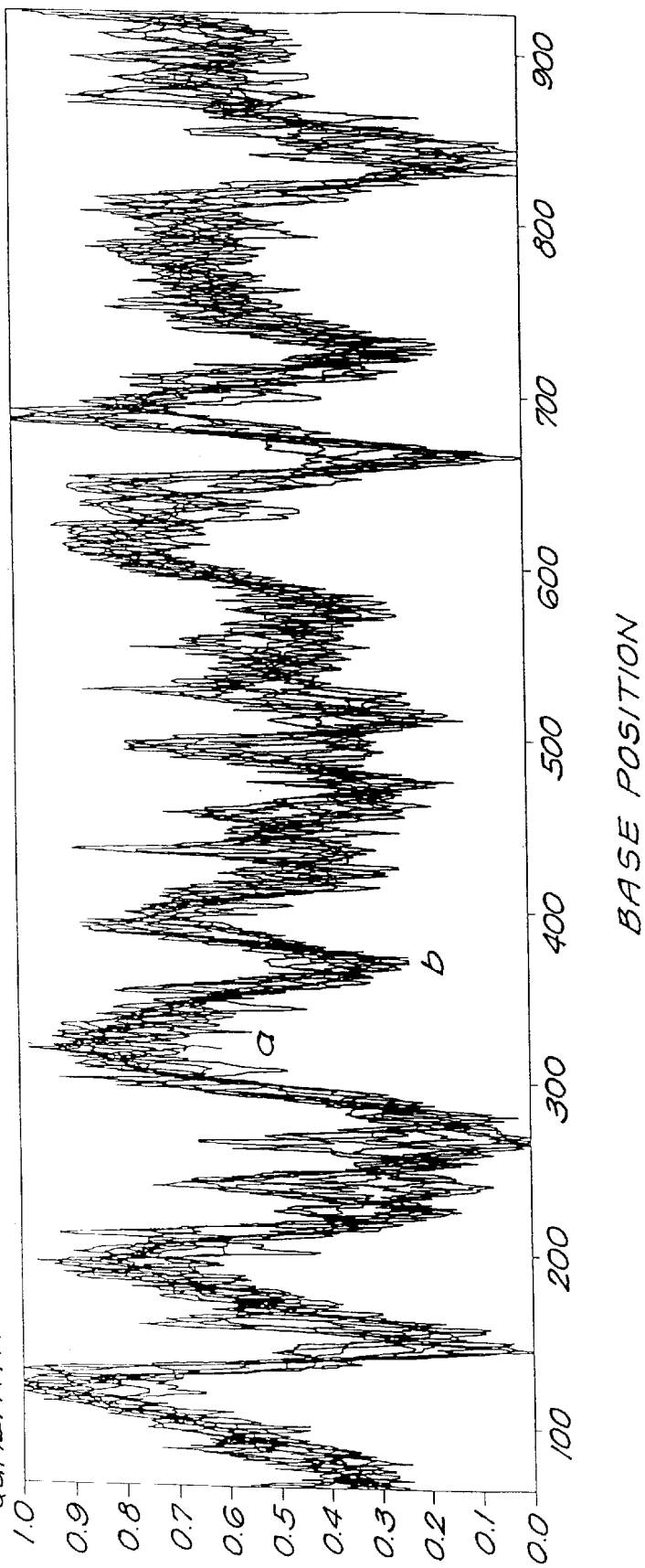
FIG. 2 is an overlaid plot of the data shown in FIG. 1.

(4) [Optional step] Overlapping Energy Contours Constructed with Different Window Sizes: A more direct comparison of these energy contours is to "overplot" (e.g., plot one data set over another) them as shown in FIG. 2. Features of the distribution of melting stability are clearly apparent and apparently only slightly dependent on window size over the range examined. Regions of lowest magnitude are the least stable while regions of highest magnitude are the most stable. Although the same general features are observed on all the distribution function shown in FIG. 2, there are small deviations (on the order of 10–20%) about what appears to be the "average" shape of the distribution. These distribution directly reveal the contributions of hydrogen bonding and nearest-neighbor stacking to DNA stability. The prominent features of the distribution are generally determined by the amount of A-T or G-C type bps in the sequence. For example, the peaks in the overlaid plots of FIG. 2 depict regions relatively higher in G-C percentage. The converse is true for the "valleys," which reveal a larger percentage of A-T type base pairs in that region. Because of the greater relative energy of the peaks as compared to the valleys, the effect of window size is more pronounced at the peaks.

Figure 3:
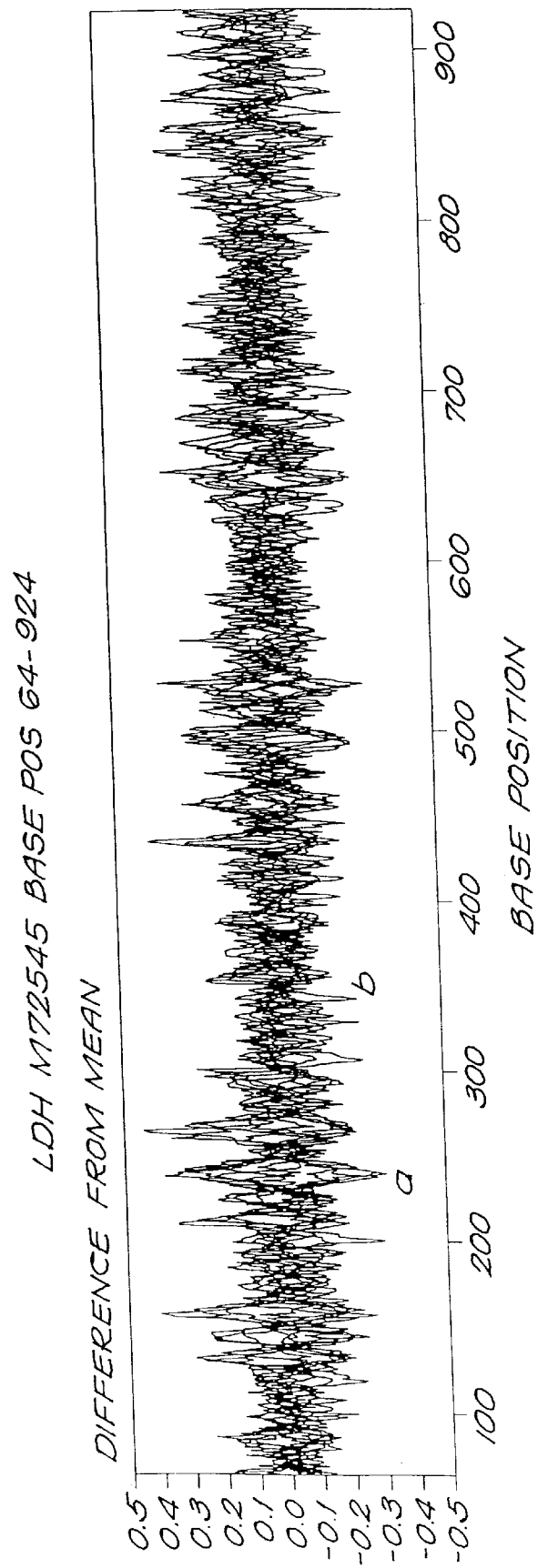
FIG. 3 is a plot of the variability of energy distributions along the representative DNA sequence.

(5) Deviations from the Window Size Average Reveal Targetable Regions: The superimposed "noise" or deviations from the mean behavior of the distribution for the different window sizes seen in FIG. 2 reveals the influence of nearest-neighbor stacking on DNA stability. It is this noise pattern that can be isolated. To better examine this component of the distribution functions, the average over all normalized energies determined for each window size are determined at each bp position, s. That is, $$<\Delta G^W>_{ave}(s) = \Sigma_j <\Delta G_j^w>(s)/N_w$$

where $N_w$ is the number of window sizes. Now the differences, $$\delta<\Delta G^w>_{ave}(s) = <\Delta G^w>_{ave}(s) - <\Delta G_j^w>(s)$$

are determined and plotted vs sequence position for each window size as shown in FIG. 3. The result is a "noise" pattern with most values between –0.20 and +0.20 centering around 0 along the bp position. Notably, several regions emerge from this pattern which display larger range than the preselected noise criteria. These regions are clearly seen in FIG. 3 (e.g., the point labelled "A" in FIG. 3 has large variability) and display the highest variability in sequence dependent stability with changes in window size and after scaling the values for the entire sequence set as described above. These are the desired targets for sequence specific anti-sense therapeutics.

(6) Selection of Sequences: The 200 base sequences (other lengths, e.g., 150, 100, or 50 bases, can also be used), 100 to either side of the "variational maxima" seen on the plots of $\delta<\Delta G^w>_{are}(s)$ vs. s ($\delta<\Delta G^w>_{ave}(s)$) are identified from the mRNA sequence and subjected to further examination. While these 200-mers could be used as anti-sense oligonucleotides immediately it is more desirable to use smaller oligomers comprising, e.g., approximately 50, 40, 30 or fewer bases that are subsequences of the selected 200-mer. Optimal anti-sense candidate oligomers within the 200-mer will contain a 2–10 bp more stable region flanked by relatively unstable regions.

In some applications it may be desirable to select sets of anti-sense oligonucleotides all with a pre-defined optimal duplex free-energy but with different variable lengths. This is done by scanning the energetic distribution of the 200 bp region and determining the various pieces from 15 to 30 bps in length that have the same calculated free-energy of stability.

In other applications it may be desirable to select sets of isoenergetic anti-sense candidates of a given length. This is done by scanning the energetic distribution of the 200 bp region and determining the various pieces of a given length that have the same calculated free-energy.

In other applications it may be desirable to choose antisense oligonucleotides of a preselected melting temperature, $T_m$. This can be done using the formula, $$T_m = (\Delta H_D + \Delta H_{nue})/)\Delta S_D + \Delta S_{nue} + ln(\alpha C_T)$$

Where $\Delta H_D$ and $\Delta S_D$ are the calculated melting enthalpy and entropy for the particular sequence.

The entropy of nucleation is $\Delta S_{nue}$ and is regarded as a constant for a particular type of target in our equational formulation. That is, it does not depend on oligomer length. In contrast, the enthalpy of duplex nucleation, $\Delta H_{nue}$ is primarily electrostatic in nature and therefore depends on sequence length, G-C percentage and salt concentration. The total strand concentration is $C_T$ and $\alpha$ is a factor that properly accounts for sequence degeneracies in association of the oligomers. Overall, stability of the chose oligomers can therefore be adjusted by changes in G-C percentage and length.

While the invention has been described with reference to selection of sequences which are suitable targets for the design of antisense oligonucleotides, it will be appreciated that the methods described herein can be used to identify regions of a target nucleic acid sequence (including, but not limited to, a coding or non-coding DNA or RNA) which are suitable for interaction with other ligands which can bind to the nucleic 30 acid, including one or more of: a compound which binds to a nucleic acid in a sequence-specific way (e.g., a sequence specific cleavage enzyme, such as a restriction endonuclease, including EcoRI, HaeIII, BamHI and BglI, or an enzyme or other molecule which binds to a specific sequence, e.g., molecules which modulate the expression of a product encoded by a nucleic acid) or in a sequence-non-specific way (e.g., DNaseI or micrococcal nuclease); a protein; an enzyme; an enzyme or other molecule (and agonists or antagonists thereof) which alters the structure of a nucleic acid to which is binds, e.g., by breaking or forming a covalent or non-covalent bond, e.g., a hydrogen bond, between an atom of the nucleic acid and another atom, e.g., an atom of the same strand, an atom of the complementary sequence, or an atom of another molecule; an enzyme which cleaves one or both strands of the nucleic acid, and agonists or antagonists thereof; an enzyme which methylates or alkylates the nucleic acid. and agonists or antagonists thereof; an enzyme which promotes or catalyzes the synthesis of a nucleic acid, e.g., a polymerase which requires a double stranded prime, and agonists or antagonists thereof, a DNA polymerase, e.g., DNA polymerase I or Taq polymerase, and agonists or antagonists thereof; an enzyme which alters the primary or secondary structure of a nucleic acid, e.g., a topoisomerase, or an enzyme related to recombination or replication, and agonists or antagonists thereof, a DNA binding ligand, and agonists or antagonists thereof; a mutagen; a compound which enhances gene expression, and agonists or antagonists thereof; a compound which intercalates into a double stranded nucleic acid, and agonists or antagonists thereof; a compound which, when contacted with a reaction mixture comprising a first single stranded nucleic acid and a second single stranded nucleic acid will accelerate the rate of duplex formation at least n-fold, wherein n is an integer between 2 and 1,000, inclusive; a compound which will decrease the free energy of duplex formation by n-fold, wherein n is an integer between I and 1,000 inclusive; a small molecule, e.g., any metalloorganic compound, any heterocyclic compound, or any protein which binds a nucleic acid; proteins or other molecules which are associated with the structural organization of DNA in the cell nucleus, or the packaging of DNA, including histones and nucleosomes; nucleic acid binding mutagens or carcinogens, or agonists or antagonists thereof, viral proteins and agonists or antagonists thereof. Thus, the methods of the invention have broad applicability.

Those skilled in the art will recognize, or be able to ascertain using no more than routine experimentation, numerous equivalents to the specific procedures described herein. Such equivalents are considered to be within the scope of this invention and are covered by the following claims.

The contents of all references and patent applications cited herein are hereby incorporated by reference.

Other embodiments are within the following claims.

What is claimed is:

1. A method of identifying sites on a nucleic acid sequence having a desired melting free energy variability comprising:

providing a nucleotide sequence;

calculating a melting free energy of a plurality of windows centered on a base pair for a plurality of base pairs from the nucleotide sequence, wherein said plurality of windows are of a size between 2 and Y, wherein Y is an integer between 3 and 100;

for each window size, constructing a melting free energy distribution along the sequence, normalizing the distribution to a standard scale;

determining mean normalized melting free energy values for all windows for each base pair position; and providing the deviation from the mean normalized melting free energy value of each base position for each window at the same base position; and selecting the sites with the largest deviation as the sites having the desired melting free energy variability.

2. The method of claim 1, wherein the plurality of base pairs comprises at least 50% of the base pairs of the nucleotide sequence.

3. A method of identifying optimized ligand binding sites on a nucleic acid sequence, the method comprising:

providing a nucleic acid sequence;

calculating melting free energy values for at least two window sizes at each of a plurality of base pairs of the nucleic acid sequence;

normalizing said melting free energy values for each window size at each base pair To a standard scale;

calculating a deviation of the normalized melting free energy value for each window size at a base pair from a mean normalized melting free energy value at the same base pair;

selecting a base pair at which a large deviation from the normalized melting free energy value is calculated, relative to at least one other base pair;

such that optimized ligand binding sites on the nucleic acid sequence is identified.

* * * * *